(12) United States Patent
Wall et al.

(10) Patent No.: US 9,289,250 B2
(45) Date of Patent: Mar. 22, 2016

(54) EXTENDER COLLAR SYSTEM

(75) Inventors: Daniel Paxton Wall, Medina, TN (US);
Richard Quinn Brown, Collierville, TN (US); Kevin T. Foley, Germantown, TN (US); Joseph D. Shine, Germantown, TN (US); Gregory C. Marik, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 66 days.

(21) Appl. No.: 13/274,702

(22) Filed: Oct. 17, 2011

(65) Prior Publication Data

US 2013/0096635 A1 Apr. 18, 2013

(51) Int. Cl.
| | |
|---|---|
| *A61B 17/58* | (2006.01) |
| *A61B 17/60* | (2006.01) |
| *A61F 2/00* | (2006.01) |
| *A61B 17/70* | (2006.01) |
| *A61B 17/88* | (2006.01) |
| *A61B 19/00* | (2006.01) |

(52) U.S. Cl.
CPC ........... *A61B 17/7085* (2013.01); *A61B 17/708* (2013.01); *A61B 17/7079* (2013.01); *A61B 17/7076* (2013.01); *A61B 17/7091* (2013.01); *A61B 17/8875* (2013.01); *A61B 2019/307* (2013.01); *A61B 2019/444* (2013.01); *A61B 2019/461* (2013.01); *A61B 2019/462* (2013.01); *A61B 2019/467* (2013.01)

(58) Field of Classification Search
CPC ......... A61B 17/17; A61B 17/58; A61B 17/92
USPC .................... 606/96, 99, 104, 86 A
See application file for complete search history.

(56) References Cited

U.S. PATENT DOCUMENTS

| | | | |
|---|---|---|---|
| 7,811,288 B2 | 10/2010 | Jones et al. | |
| 7,967,821 B2 | 6/2011 | Sicvol et al. | |
| 8,236,032 B2 * | 8/2012 | Ramsay et al. ............... | 606/279 |
| 8,308,729 B2 * | 11/2012 | Nunley ............. | A61B 17/7086 606/79 |
| 2002/0116009 A1 * | 8/2002 | Fraser ................... | A61F 2/4611 606/99 |
| 2002/0198533 A1 * | 12/2002 | Geisler et al. .................... | 606/96 |
| 2007/0233079 A1 * | 10/2007 | Fallin et al. ...................... | 606/61 |
| 2008/0077135 A1 * | 3/2008 | Stad et al. ........................ | 606/61 |
| 2008/0091213 A1 | 4/2008 | Jackson | |
| 2008/0114403 A1 | 5/2008 | Kuester et al. | |
| 2008/0125817 A1 | 5/2008 | Arnett et al. | |
| 2009/0099605 A1 | 4/2009 | Fallin et al. | |
| 2010/0114179 A1 * | 5/2010 | Moore ............... | A61B 17/7032 606/308 |
| 2011/0040328 A1 | 2/2011 | Miller et al. | |

* cited by examiner

*Primary Examiner* — Ellen C Hammond
*Assistant Examiner* — Christina Negrellirodriguez

(57) ABSTRACT

A collar for extenders and an extender assembly including a collar is disclosed. The collar is configured to receive extenders and maintain the extenders in a parallel orientation so as to prevent splaying and premature beak-off of the extenders from the spine. Methods of use are disclosed.

19 Claims, 12 Drawing Sheets

US 9,289,250 B2

EXTENDER COLLAR SYSTEM

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Surgical treatments used for positioning and alignment may employ implantable rods and fasteners. Surgical instruments, such as, for example, extenders are employed to position and align the implantable rods and fasteners with a spine. This disclosure describes an improvement over these prior art technologies.

SUMMARY OF THE INVENTION

Accordingly, a collar configured to attach to the proximal end of extenders so as to prevent splaying of the extenders and provide a passageway for surgical instruments, such as screwdrivers and measuring devices, is provided. An extender system that contains both extenders and the collar is provided for delivery of an implant, such as bone fasteners and rods, to a surgical site for treatment of spine related conditions. The collar is configured to connect to a proximal end of an extender and includes a body defining a longitudinal axis. The body also includes an outer surface and an inner surface configured to define a first cavity, a second cavity and an intermediate cavity disposed therebetween. The inner surface including at least one wall projecting therefrom and being disposed about the intermediate cavity, wherein the first and second cavities receive the proximal end of the extenders to prevent splaying and the intermediate cavity includes a passageway configured for disposal of a surgical instrument.

In an embodiment in accordance with the principles of the present disclosure, an extender system including first and second extenders extending between a proximal end and a distal end along a longitudinal axis is provided. The first and second extenders are positioned so as to form an inner cavity along the longitudinal axis with openings at the proximal and distal ends. The distal end of the first and second extenders are configured to attach to anchors engageable to a spinal column of a patient and the proximal end includes at least one detent. Also included in the extender system is a collar having a body defining a longitudinal axis, an outer surface and an inner surface configured to define a first cavity, a second cavity and an intermediate cavity disposed therebetween. The inner surface including at least one wall projecting therefrom and being disposed about the intermediate cavity wherein the first and second cavities receive the proximal end of the extenders to prevent splaying and the intermediate cavity includes a passageway that aligns with the inner cavity formed by the first and second extenders that is configured for disposal of a surgical instrument.

In an embodiment in accordance with the principles of the present disclosure, a surgical kit including a collar configured for connection to a proximal end of an extender is provided. The kit also includes at least two extenders extending between a proximal end and a distal end along a longitudinal axis forming an inner cavity along the longitudinal axis. The inner cavity having openings at the proximal and distal ends and the distal end of the extenders configured to attach to anchors engageable to a spinal column of a patient. Hardware to be used with the extender system of the kit such as bone fasteners, screws, and capped rods are also included. The kit may also include instruments used with the extender system such as screwdrivers and measuring devices, for use in surgical procedures for the spine.

The extender kit provided in accordance with the principles of the disclosure may be used for surgical procedures of the spine. The kit provides the tools for placement of an implant, for example capped rods or bone fasteners, in the spine of a patient. One method in which the extenders system can be used includes attaching the distal end of the extenders to fasteners positioned in the spine of a patient so as to secure the distal ends of the extender to the spine of a patient. Once the extenders are in place the collar is attached to the proximal end of the extenders in order to stabilize the extenders and keep them substantially to each other so as to prevent splaying and to provide an inner cavity between the extenders for the passage of implants and surgical instruments. The collar can be attached to the extenders either before or after the implant is introduced into the inner cavity of the extenders. Once the implant is positioned within the inner cavity along the longitudinal axis of the extenders, the implant is advanced towards the spine of a patient for attachment. Throughout the procedure, the collar keeps the extenders parallel to one another so as to prevent splaying and stabilize the extenders.

BRIEF DESCRIPTION OF THE DRAWINGS

The present disclosure will become more readily apparent from the specific description accompanied by the following drawings, in which.

Like reference numerals indicate similar parts throughout he figures.

DETAILED DESCRIPTION OF THE INVENTION

Figure 1:
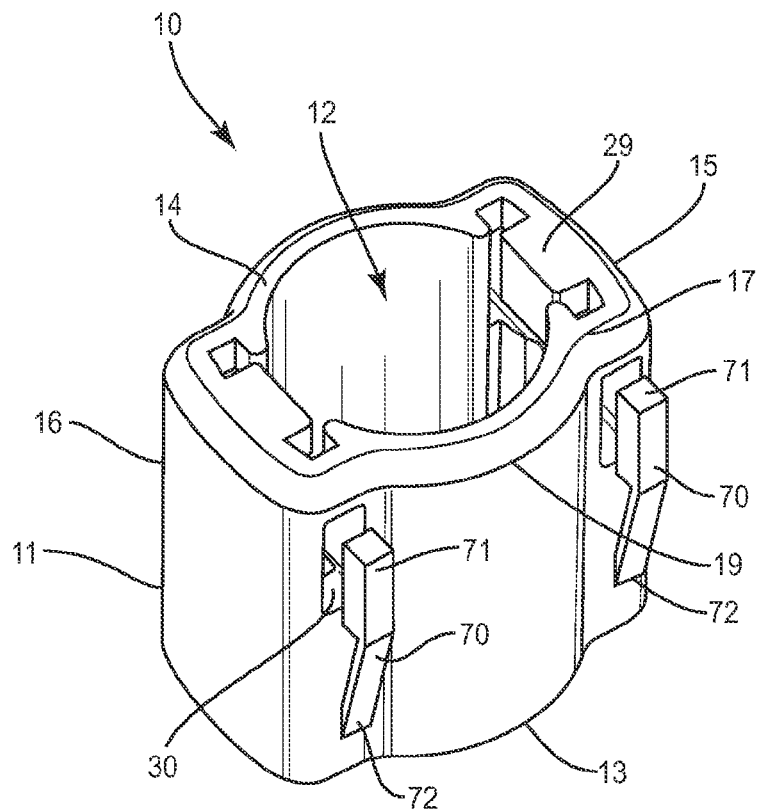
FIG. 1 is a perspective view of one particular embodiment of the collar showing the proximal end in accordance with the principles of the present disclosure.
Figure 2:
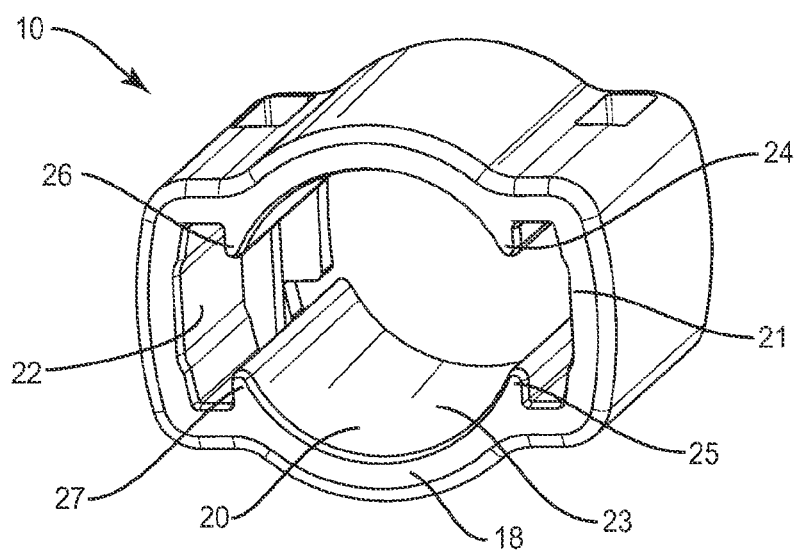
FIG. 2 is a perspective view of the collar shown in FIG. 1 showing the distal end in accordance with the principles of the present disclosure.
Figure 3:
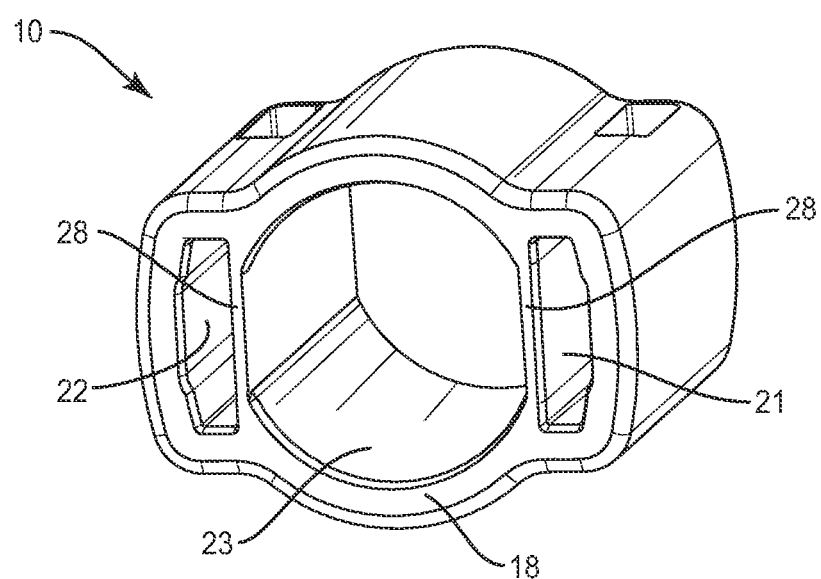
FIG. 3 is a perspective view of the collar shown in FIG. 1 showing three separate cavities in accordance with the principles of the present disclosure.
Figure 4:
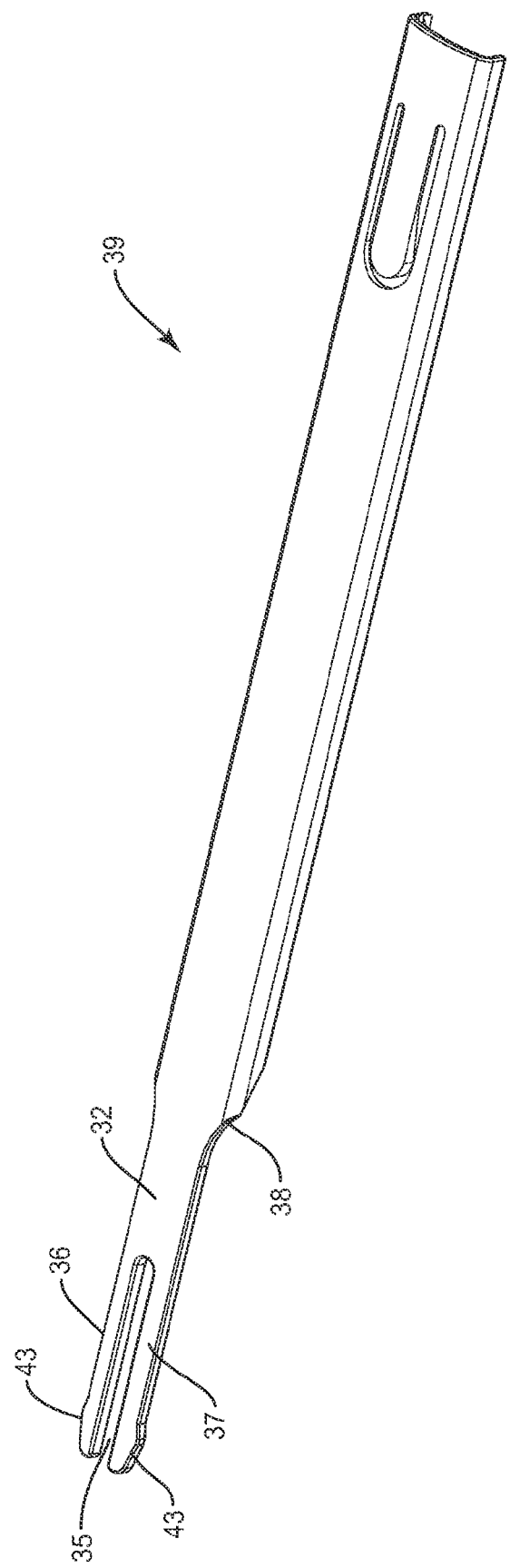
FIG. 4 is a perspective view of an extender configured to mate with the collar shown in FIG. 1 in accordance with the principles of the present disclosure.
Figure 5:
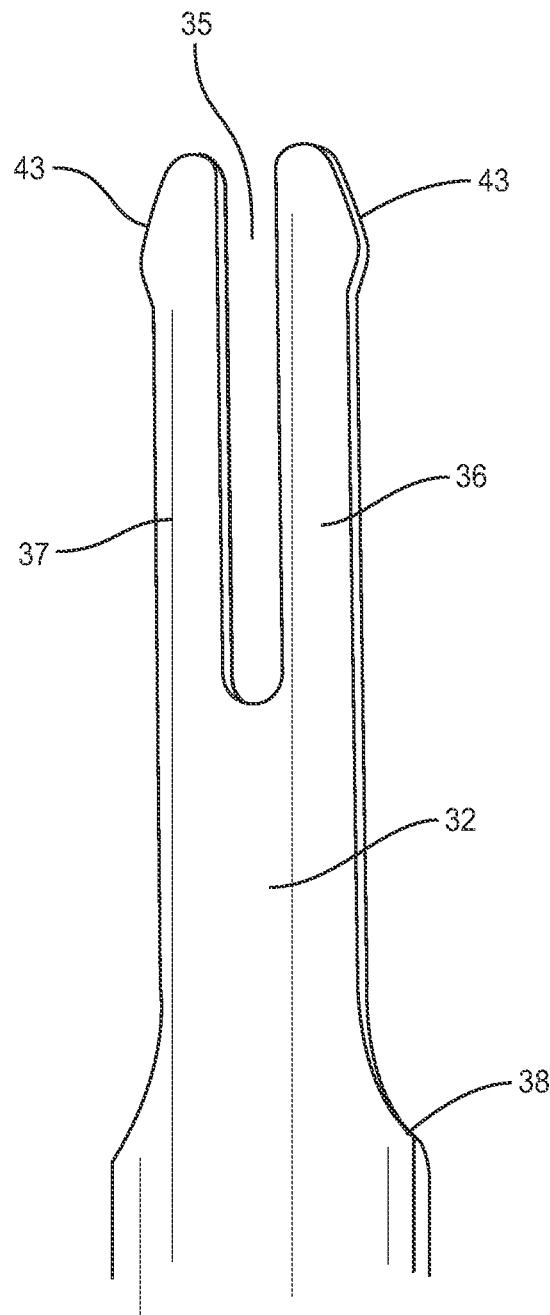
FIG. 5 is a prospective view of the proximal end of the extender shown in FIG. 4 in accordance with the principles of the present disclosure.
Figure 6:
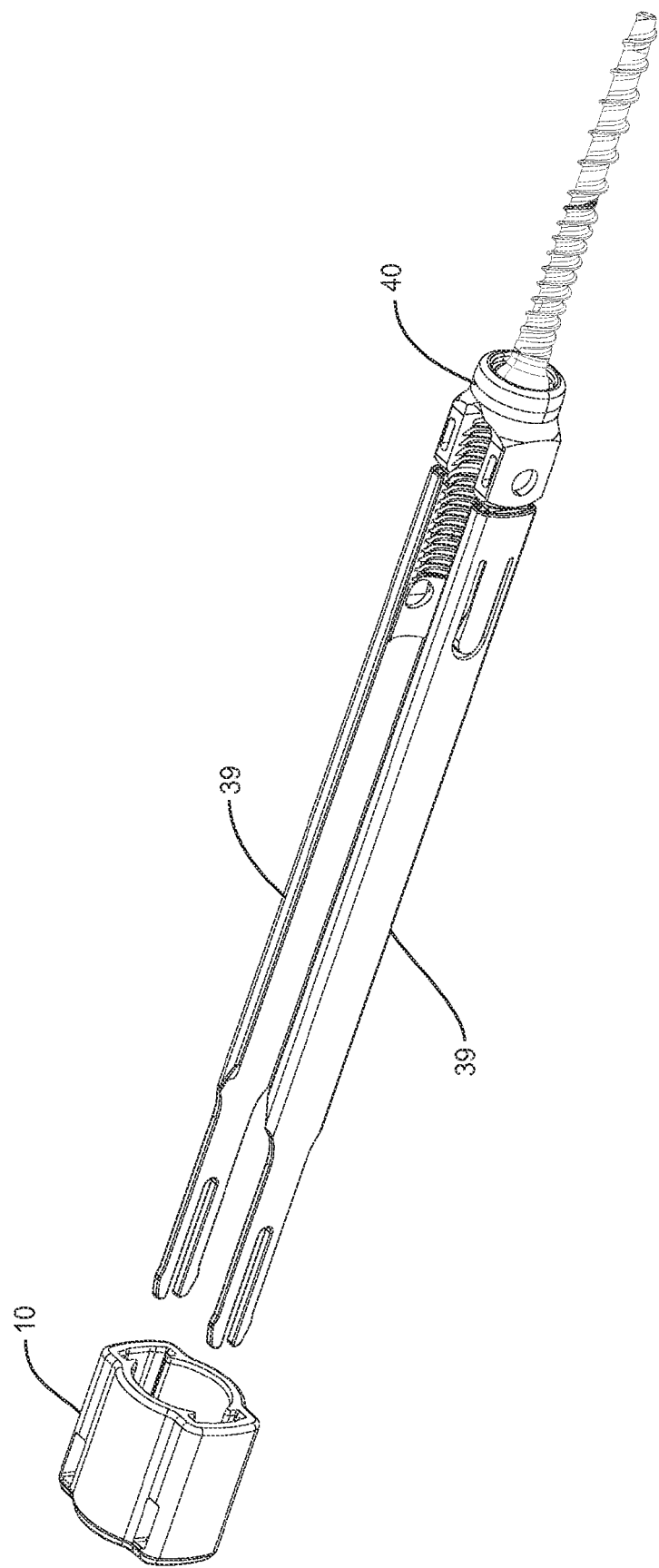
FIG. 6 is a perspective view of a collar cap and two extenders attached to a screw assembly in accordance with the principles of the present disclosure.
Figure 7:
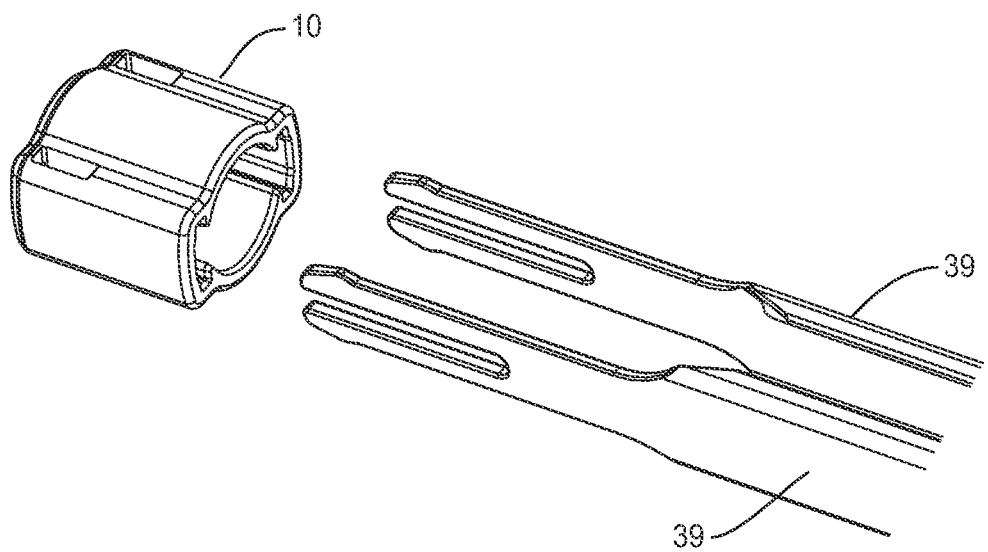
FIG. 7 is a perspective view of the proximal end of the extender and collar shown in FIG. 6 aligned for attachment in accordance with the principles of the present disclosure.
Figure 8:
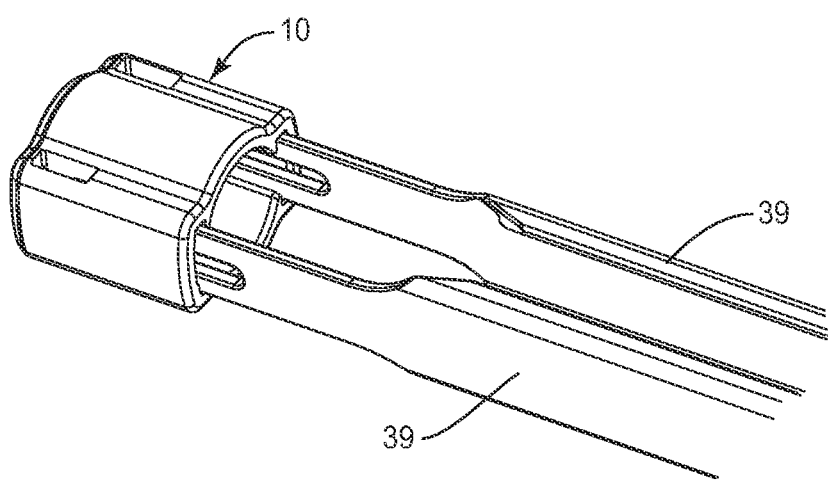
FIG. 8 is a perspective view of the proximal end of the extender and collar shown in FIG. 7 with the collar in the process of attachment in accordance with the principles of the present disclosure.
Figure 9:
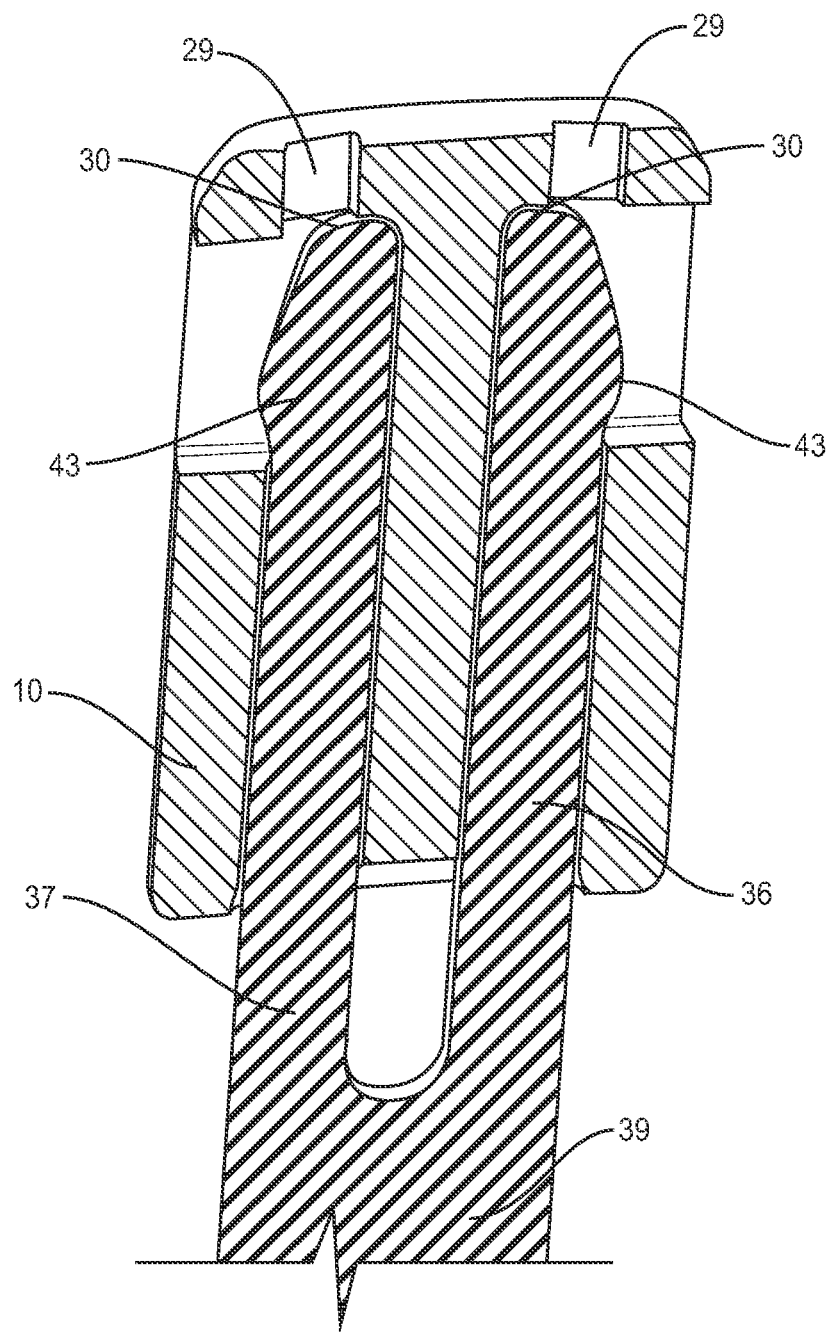
FIG. 9 is a cross-sectional view of the proximal end of the extender and collar shown in FIG. 8 with the collar attached in accordance with the principles of the present disclosure.
Figure 10:
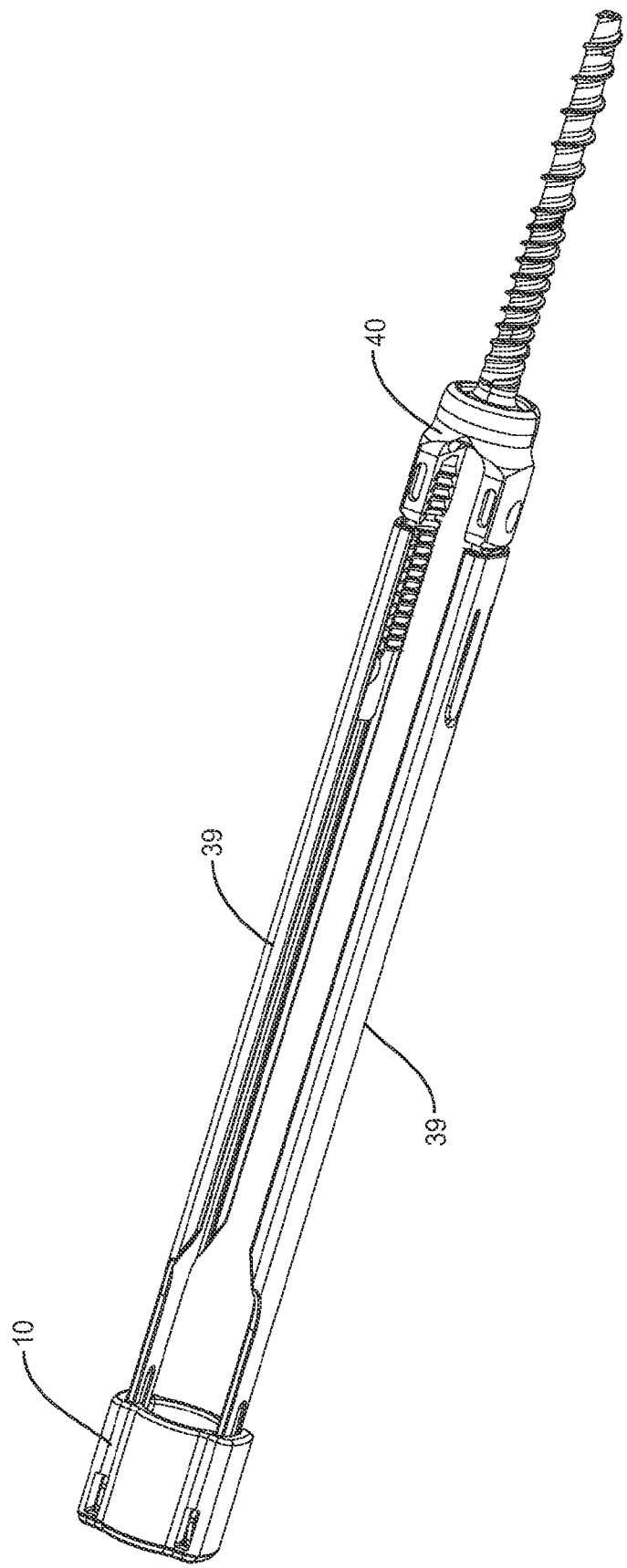
FIG. 10 is a perspective view of the surgical instrument with the collar engaged in accordance with the principles of the present disclosure.
Figure 11:
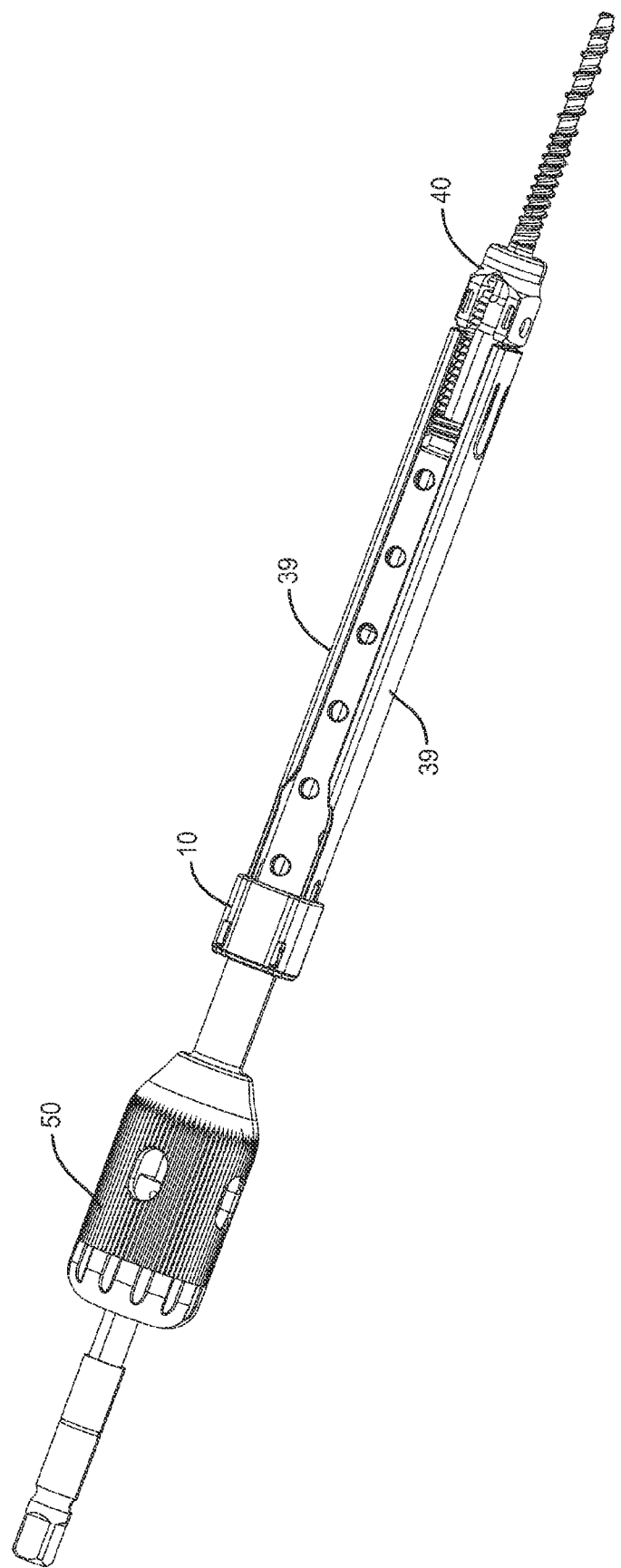
FIG. 11 is a perspective view of the surgical instrument of FIG. 10 aligned with a screwdriver in accordance with the principles of the present disclosure.
Figure 12:
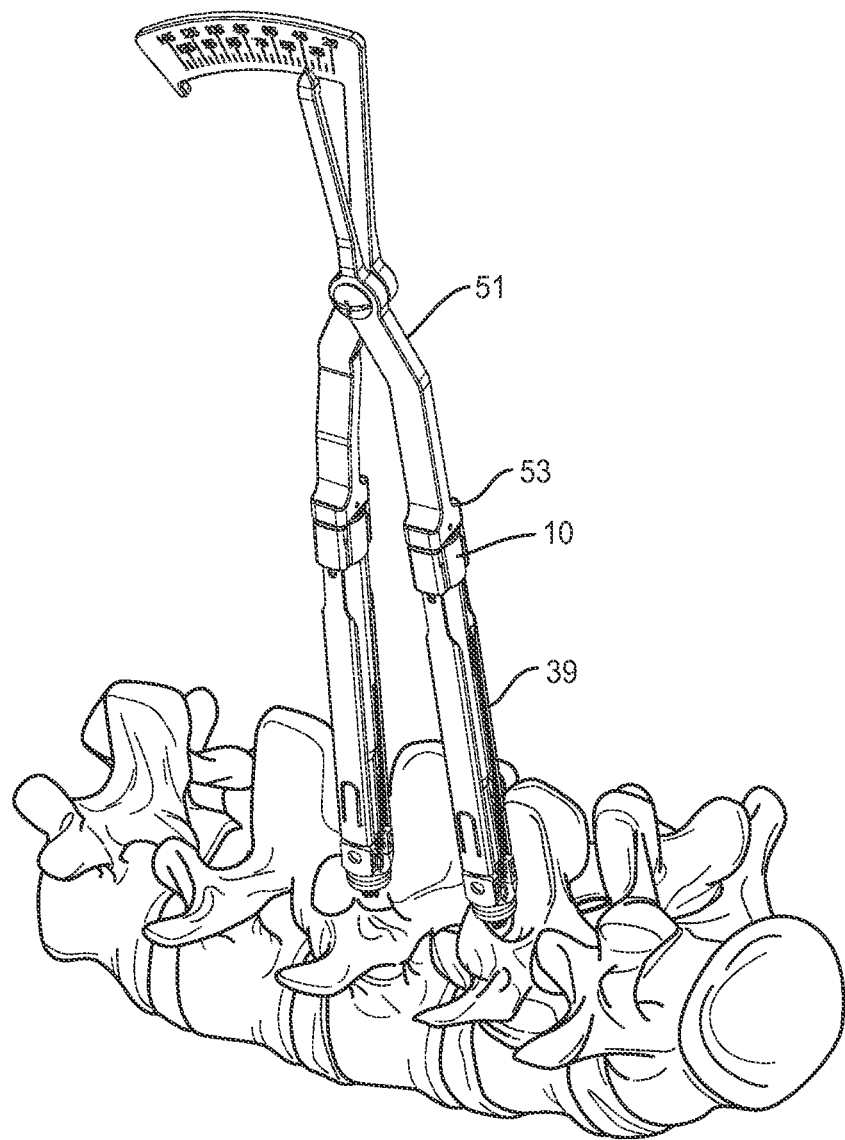
FIG. 12 is a perspective view of the surgical instrument of FIG. 10 aligned with a rod measuring device in accordance with the principles of the present disclosure.

The exemplary embodiments of the collar, and the extender system including the collar, are discussed in terms of medical devices for the treatment of musculoskeletal disorders and more particularly, in terms of extenders and surgical instruments for implant delivery to a surgical site for treating a spine. It is envisioned that the collar attaches to the proximal end of the extenders so as to keep the extenders parallel to one another so as to prevent splaying and premature break-off of the extenders. The extender system can be used to introduce an implant, such as a rod or a bone fastener, for attachment to a spine. In one embodiment, a kit is provided that includes the extenders, collar, implants, such as rods and fasteners, and may also include specific surgical instruments to be used with the extender system for attachment of the implants to the spine of a patient. One or all of the components of the extender system can be disposable, peek packed, pre-packed sterile devices, or reusable.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific instruments, devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a", "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a collar configured for attachment to the proximal end of extenders, an extender system containing the collar, a kit containing the extender system and implants and surgical instruments used with the extender system. Alternate embodiments are also disclosed. Reference will now be made in detail to the exemplary embodiments of the present disclosure, which are illustrated in the accompanying figures. Turning now to FIGS. 1-14, there is illustrated components of a collar and an extender system including the collar in accordance with the principles of the present disclosure.

The components of the collar and extender system can be fabricated from biologically acceptable materials suitable for medical applications, including metals, synthetic polymers, ceramics and bone material and/or their composites, depend-ing on the particular application and/or preference of a medical practitioner. For example, the components of the collar and extender system, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the system may have material composites, including the above materials, to achieve various desired characteristics such as strength, rigidity, elasticity, compliance, biomechanical performance, durability and radiolucency or imaging preference. The components of the collar and surgical instrument, individually or collectively, may also be fabricated from a heterogeneous material such as a combination of two or more of the above-described materials. The components of the collar and surgical instrument may be monolithically formed, integrally connected or include fastening elements and/or instruments, as described herein.

The extender system of the disclosure includes a collar as shown in FIGS. 1-14. The collar includes a body 11 having a proximal end 14 and a distal end 13 that defines the shape of the collar 10. It is envisioned that the body may have alternate cross section configurations, such as, for example, oval, oblong, triangular, rectangular, square, polygonal, winged, irregular, uniform, non-uniform, c-shaped, variable and/or tapered as long as it is configured to fit on the proximal end of an extender so as to prevent splaying of the extenders. Body 11 has an inner surface configured to define a first cavity 21, a second cavity 22 and an intermediate cavity 23 disposed therebetween. The intermediate cavity 23 extends along the longitudinal axis from a proximal end 14 to a distal end 13 of the collar 10. The intermediate cavity 23 is configured to receive instruments and/or implants used in the surgical procedure.

First and second cavities 21, 22 extend from the proximal end 14 to the distal end 13 of collar 10 and are configured to receive the proximal ends of extenders. That is, the first and second cavities 21, 22 have a width and height greater than the width and height of the extender it is configured to receive. The width and height of first and second cavities 21, 22 can vary from collar to collar depending on the width and height of the extenders to be received. For example, the height of first and second cavities 21, 22 ranges from about 4.0 mm to about 7.5 mm and the width of first and second cavities 21, 22 ranges from about 1.0 mm to about 3.25 mm. The depth of first and second cavities 21, 22 can also vary depending on the desired overall length of the collared extenders. Since the extender system including the collar is used in open surgery, mini-open surgery and minimally invasive surgery, the surgeon may use the proximal end of the collar 14 positioned on an extender to gauge whether a surgical instrument in the passageway 12 of the intermediate cavity 23 is fully seated. That is, the proximal end 14 of the collar 10 can be used by a surgeon as a reference point to line up a mark on the inserted instrument to determine whether the instrument is properly seated in the spine.

In an embodiment, in accordance with the principles of the present disclosure, one or both of first and second cavities has a stop member 29 positioned at the proximal end 14 of the cavity. Stop member 29 can be a separate insert that fits in first and/or second cavities, or can be a protrusion or solid block configured to contact the proximal end 32 of an extender 39 received within the first and/or second cavities. Contact of extender 39 with stop member 29 prevents extender 39 from extending pass the proximal end 14 of collar 10. This assures proper placement of the extenders 39 within the collar 10 and defines a reproducible overall length of the surgical instrument having the extenders 39 positioned within collar 10. Stop member 29 prevents extenders 39 from extending pass the proximal end 14 of cap 10 and sliding down the extenders 39.

In one embodiment, in accordance with the principles of the present disclosure first and second cavities 21, 22 are at least partially separated from intermediate cavity 23 by ridges formed in inner surface 20. That is, first cavity 21 is defined on one side by a portion of the inner surface 20 that spans along a first side 16 and on the other side by a partial well formed by en upper ridge 26 positioned across from lower ridge 25 on the inner surface 20. Ridges 24, 25 together partially separate first cavity 21 from intermediate cavity 23 and provide an area configured to receive and retain extenders 39 in a parallel configuration. Similarly, second cavity 22 is defined on one side by a portion of the inner surface 20 that spans along a second side 15 and on the other side by a partial wall formed by an upper ridge 26 positioned across from lower ridge 27 on the inner surface 20. Ridges 26, 27 together partially separate second cavity 22 from intermediate cavity 23 and provide an area configured to receive and retain extenders 39 in a parallel configuration.

In an alternative embodiment, in accordance with the principles of the present disclosure first and second cavities 21, 22 are completely separated from intermediate cavity 23 by left and right walls 28 extending from an upper portion of inner surface 20 to a lower portion of inner surface 20. Walls 28 completely separate first and second cavities 21, 22 from intermediate cavity 23 and as formed first and second cavities 21, 22 are configured to receive and retain extenders 39 so as to maintain the extenders in a parallel orientation to one another. The width of first and second cavities 21, 22 may vary, however in order to accommodate the proximal ends of the extenders they must be at least as wide as the width of extenders 39.

Body 11 includes at least one notch 30 configured to receive at least one detent 43 located on the proximal end 32 of extenders 39. Notch 30 can be configured to extend through body 11 from the inner surface 20 to the outer wall 19. In this configuration, detent 43 positioned within notch 30 is visible from outer wall 19. In an alternative embodiment, notch 30 can be configured so as to not breach outer wall 19 of body 11. In this configuration, detent 43 is not visible from the outer wall. In either configuration, it is envisioned that notch 30 is located in either one or each of first and second cavities 21, 22 and are configured to mate with detent 43 located on the proximal end 32 of extenders 39. Once the extenders 39 are slid into first and second cavities 21, 22 the detents 43 located on the proximal end 32 of the extenders 39 snap into notch 30. This mating relationship retains the extenders 39 within first and second cavities 21, 22 in a parallel orientation to one another so as to prevent splaying. Preventing splaying of the extenders assures that the extenders 39 do not prematurely break off from the fasteners.

Extenders 39 extend between a proximal end 32 and a distal end 38 along longitudinal axis. It is contemplated that the thickness of extenders 39 may be uniformly increasing or decreasing, or have alternate diameter dimensions along longitudinal axis. It is further contemplated that all or only a portion of extenders 39 have a uniform width along the longitudinal axis. In one embodiment, extenders 39 have a reduced width at the proximal end 32 as compared to the rest of extenders 39. It is contemplated that the transition between the two different widths can be gradual, abrupt or can be defined by shoulder 37 that gradually flares outwardly from the narrower width to the greater width over a relatively short distance. The proximal end 32 of extenders 39 having the reduced width contains first and second tongs 36, 37 having one or more detents 43 that are, as stated herein, configured to mate with notch 30. It is contemplated that detent 43 can have various shapes, such as, curved, rectangular, square, pointed, uniform or irregular shaped and protrudes away from the surface of tongs 36, 37. The shape of detent 43 is configured so that it snaps into notch 30 and extenders 39 are retained within the first and second cavities.

In one embodiment, proximal end 32 contains a first tong 36 and a second tong 37 separated by a space 35. Space 35 is defined by inner walls between first and second tongs 36, 37 and extends distally from proximal end 32. Space 35 positioned between tong 36 and tong 37 provides a flexing area in which the tongs can extend into when depressed towards one another. Once the force placed on first and second tongs 36, 37 are released, the tongs naturally spring back to their original position and space 35 is reestablished. It is contemplated that first and second cavities 21, 22 of the collar 10 are configured so that first and second tongs 36, 37 are compressed together as the extenders are advanced into first and second cavities 21, 22. Once detents 43 on tongs 36, 37 mate with notch 30, tongs 36, 37 snap back to their original position releasably locking the extenders 39 to the collar 10.

In one embodiment, the cross section of first and second cavities 21, 22 gradually tapers from the distal end 13 to the proximal end 14 so that when extender 39 is advanced into first and second cavities 21, 22, detents 43 on first and second tongs ride along the inner surface and are gradually compressed towards each other. Once detents 43 come in contact with notches 30 they snap into notches 30 and first and second tongs 36, 37 flex back towards their original position and extenders 39 are locked in place. Pulling the collar 10 away from the distal end of the extenders causes the detents to release from the notches 30 and disconnects collar 10 from the extenders. That is, by pulling collar 10 away from the extenders or by directly depressing detents 43 inwardly, detents 43 release from notches 30 and the extenders can be disconnected from the collar 10. Once disconnected, the extenders 39 can be removed from the patient one by one, sterilized and used again or discarded.

It is contemplated that collar 10 can include a quick release system that facilitates release of the collar 10 from extenders 39. In one embodiment, the quick release system includes a first actuator arm 70 and a second actuator arm 71 that are each attached to outside surface 19 of collar 10 at one end 72 and have a contact surface configured to contact detent 43 at an opposite end 71. Each actuator arm is flexible and can move from a first position to a second position such that in the first position the contact end 71 is not engaged with detent 43 and in a second position contact end 71 comes in contact with the detents 43. Actuator arms 70, 71 move from the first position to the second position by compressing each actuator arm inwardly towards the outer surface 19 of collar 10 so that contact end 71 comes in contact with detents 43 extending to the outside surface of the collar. Once detents 43 are pushed back out of notches 30 and the compression force exerted on each arm is released, the arms return back to their original position and collar 10 can be detached from extenders 39. It is contemplated that the thickness of actuator arms 70, 71 may be uniformly increasing or decreasing, or have alternate diameter dimensions along the longitudinal axis. It is further contemplated that all or only a portion of the surfaces of contact end 71 may have alternate surface configurations, such as, for example, those alternatives described herein. It is envisioned that actuator arms 70 may have alternate cross section configurations, such as, for example, oval, oblong, triangular, rectangular, square, polygonal, irregular, uniform, non-uniform, variable and/or tapered.

It is also contemplated that detents 43 can be color coated so that once they are snapped into notches 30 that extend to the outside surface, the color coated detents 43 are readably visible from the outside surface. This would allow a surgeon to quickly confirm that the detents are positioned within the notches and that the collar is properly seated on the extenders 39. The color used to coat the detents should contrast the color of the outside surface of the collar so that it is easily noticed from the outside surface.

Collar 10 has a top surface 17 at the proximal end 14 and a bottom surface 18 located at the distal end 13. The top surface 17 is configured to seat instruments used with the collared extender system. It is contemplated that the top surface 17 can be flat as shown in FIG. 1 or can be configured to align and lock an instrument that is used with the collared extender system, such as a rod measuring device, in place. This seating assures alignment of the instrument in the intermediate cavity of the collar and the inner cavity of the extenders and acts as a stop so as to indicate that the instrument is fully seated in the surgical site. The top surface 17 can also act as a marking point that when aligned with markings on the instrument being advanced indicates proper seating of the instrument. For example, if a mark on an instrument being advanced is not visible over the top surface 17 of the collar, it is not properly seated and the surgeon will have to adjust the instrument until the marking becomes visible.

It is contemplated that a kit including the collar 10 and extenders 39 described herein is provided. The kit includes a collar 10 configured for connection to a proximal end of an extender and at least two extenders extending between a proximal end and a distal end along a longitudinal axis. The kit also includes hardware to be used with the extender system and may include instruments used with the system. The first and second extenders in accordance with the disclosure are configured so as to form an inner cavity along the longitudinal axis with openings at the proximal and distal ends when assembled. The distal ends of the extenders are configured to attach to anchors engageable to a spinal column of a patient and the kit includes such anchors. As stated herein hardware and implants that can be implanted into the spine in a procedure using the extender assembly described herein are also included. Examples of implants that can be included in the kit are selected from the group consisting of bone fasteners, screws, and capped rods as well other fasteners, implants and hardware for use with the assembly. It is also contemplated that the kit may include particular instruments that are used with the assembly such as screwdrivers, MAS screwdrivers, breakaway screwdrivers, rod measuring devices, as well as, other instruments that can be used with the assembly. The kit can be provided in a sterilized package ready fro use or can be in an autoclavable packaging to be sterilized prior to using the kit in surgery.

In operation, collar 10 is manipulated so that first and second cavities 21, 22 are positioned on the proximal portion of extenders 39. As collar 10 is advanced onto the extenders 39, tongs 36, 37 contact the inner surface 20 of first and second cavities 21, 23 and ride along the inner surface flexing inwardly towards each other. When detents 43 reach notches 30 in the inner surface 20 of first and second cavities 21, 22, the detents snap into place as the tongs 36, 37 return back to their original configuration. The collar 10 is then attached to the extenders 39 and the extenders are secured in a parallel orientation. Retaining the extenders parallel to one another prevents splaying which can lead to premature break away of the extenders from the spine. Once the procedure is completed and the extenders need to be removed, the collar can be removed by pulling the collar away from the extenders so that detents 43 release from notches 30 and the collar 10 can be slipped off of the extenders 39. It is also contemplated that the collar can remain on the extenders and the entire extender system can be removed with the collar attached.

Figure 13:
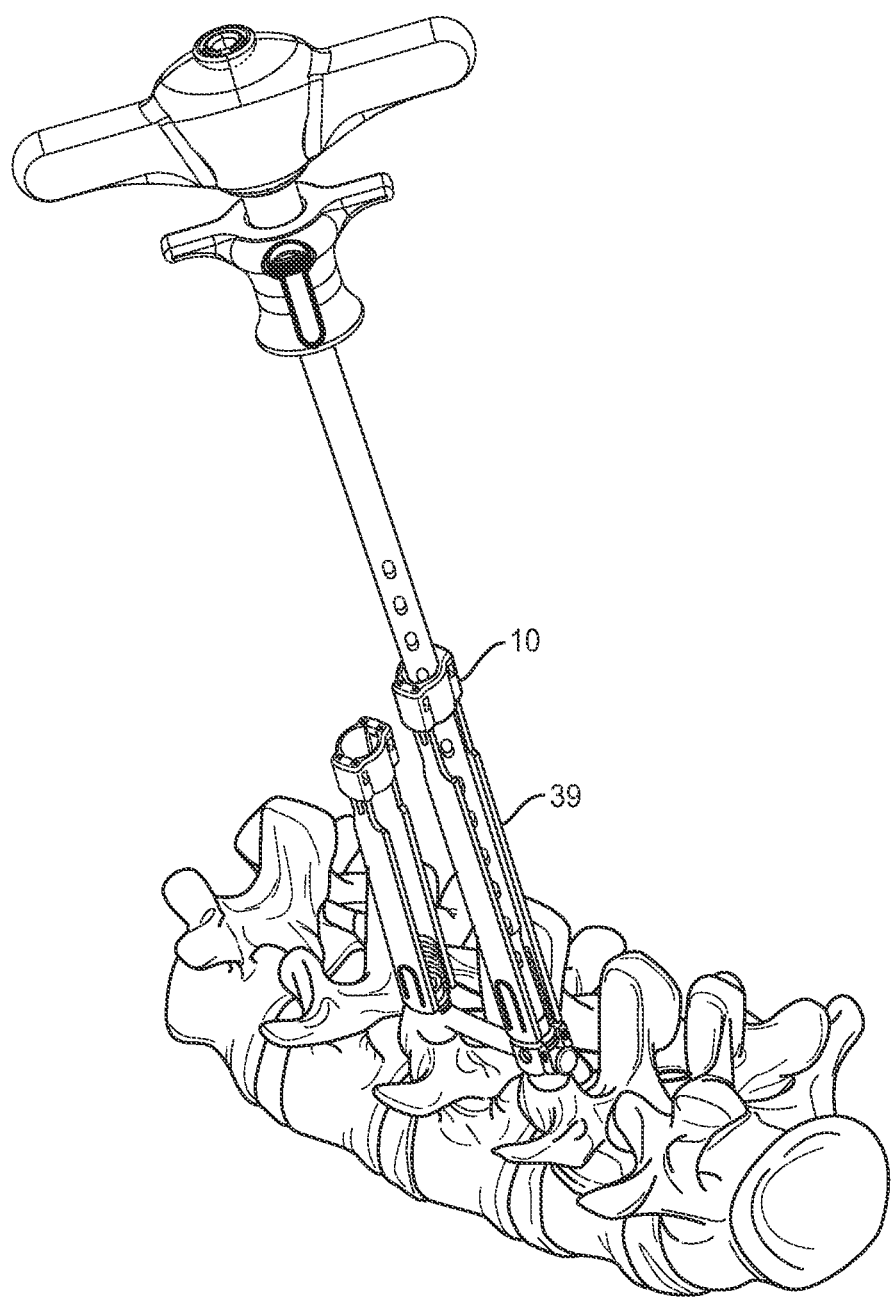
FIG. 13 is a perspective view of the surgical instrument of FIG. 10 aligned with a Break-Off Set Screw Driver in accordance with the principles of the present disclosure.

As shown in FIGS. 10-14 different instruments can be used with the collar-extender assembly. A completed collar-extender assembly can be used to place screw advanced down the inner cavity of the extenders and into the spine of a patient. A screwdriver 50 can be aligned within the inner cavity so as to advance the screw into the spine. Collar 10 aids in keeping the assembly aligned and the extenders from splaying as the screw is advanced. This feature is especially useful when the collar-extender assembly is used with a rod-measuring device 51 as shown in FIG. 13.

As shown in FIG. 13, the inserted rod-measuring device 51 is equipped with a shoulder 53 that abuts the top surface 17 of the proximal end of the collar 10. Here, the collar 10 not only keeps everything in alignment but also serves as a stop that indicates to the surgeon that the rod-measuring device is fully seated into the implants. The top surface 17 of collar 10 can also be used as a reference point for the surgeon when using instruments that do not have a shoulder to abut the collar but instead is equipped with markings on the device indicating the depth in which the instrument is inserted. When a marked instrument is used with the extender assembly of the present disclosure the surgeon can advance the instrument, such as a break-off set screw driver, into the inner cavity of the collar-extender assembly and when the line marked on the instrument is visible over or aligned with the proximal end of the collar, the device is fully seated. If the line on the device is not visible in relation to the proximal surface of the collar, then the device is fully seated. In this situation the collar not only keeps everything aligned but also serves as a reference point to align markers on instruments used with the extender assembly.

Figure 14:
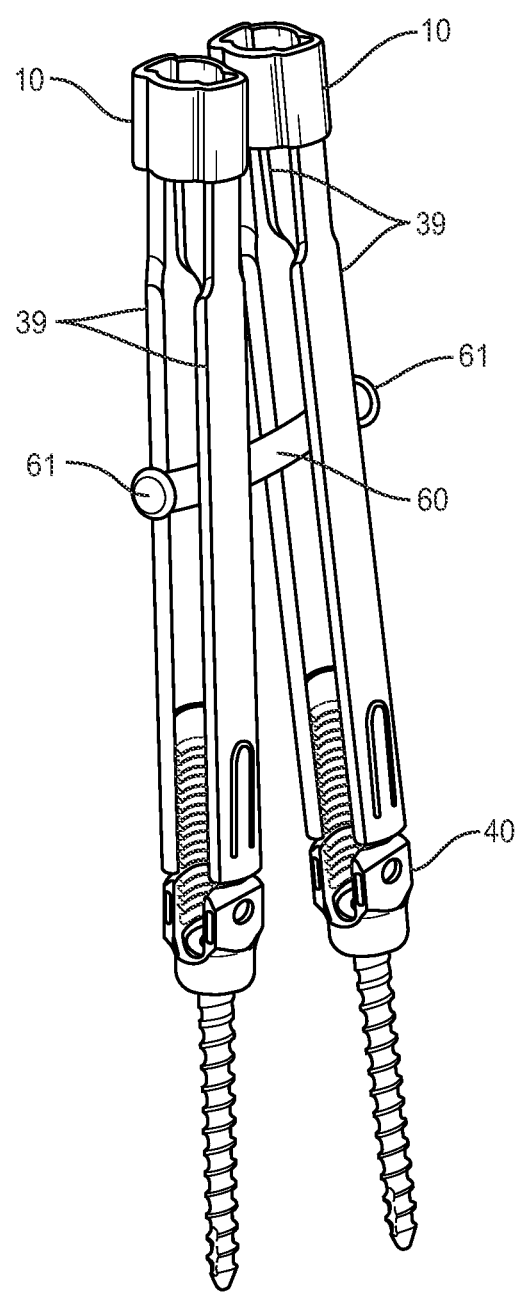
FIG. 14 is a perspective view of the surgical instrument of FIG. 10 with capped rods placed in between the parallel extenders in accordance with the principles of the present disclosure.

The collar-extender assembly can also be used to place implants into the spine of a patient. For example, as shown in FIG. 14, a capped rod 60 having capped ends 61 is positioned within the inner cavity of the extenders and is advanced towards the spine. The collar keeps the extenders parallel to one another as the implant is advanced so that the extenders serve as guide rails preventing the capped rod from coming out of the extenders as it is advanced. The collar-extender assembly also prevents splaying as the rod is advanced towards the spine thereby preventing premature splaying. It is contemplated that other surgical instruments can be used with the collar-extender assembly disclosed herein and the collar may serve additional roles in improving use of the instrument over assemblies without a collar.

In assembly, operation and use, the collar and collar-extender assembly is employed with a surgical procedure, in accordance with the principles of the present disclosure, for treatment of a spinal disorder affecting a section of a spine of a patient, as discussed herein. The collar-extender assembly is employed with a surgical procedure for treatment of a condition or injury of an affected section of the spine including cervical, thoracic, lumbar and pelvis regions of the spine.

In use, to treat the affected section of the spine, a medical practitioner obtains access to a surgical site in any appropriate manner, such as through incision and retraction of tissues in are open or mini-open surgical technique. It is envisioned that the collar-extender assembly may be used in any existing surgical method or technique including open surgery, mini-open surgery and minimally invasive surgery, whereby the spinal region is accessed through a micro-incision, or sleeve that provides a protected passageway to the area. Once access to the surgical site is obtained, the particular surgical procedure is performed for treating the spinal disorder.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A collar configured for connection to a proximal end of an extender comprising:
a body extending along a longitudinal axis between opposite proximal and distal end surfaces, the body including an outer surface and an inner surface configured to define a first cavity, a second cavity and an intermediate cavity disposed therebetween, the inner surface including at least one wall projecting therefrom and being disposed about the intermediate cavity, wherein the first and second cavities receive the proximal end of the extender to prevent splaying and the intermediate cavity includes a passageway configured for disposal of a surgical instrument,
wherein the body further comprises a stop member positioned at a proximal end of at least one of the first and second cavities such that the stop member forms a portion of the proximal end surface, the stop member being permanently fixed relative to the inner surface and configured to block at least a portion of a respective one of the first and second cavities to prevent the extender from protruding past the proximal end of at least one of the first and second cavities.

2. The collar of claim 1 wherein the first cavity is separated from the intermediate cavity by a first wall extending from an upper portion of the inner surface to a lower portion of the inner surface and the second cavity is separated from the intermediate cavity by a second wall extending from the upper portion of the inner surface to the lower portion of the inner surface.

3. The collar of claim 1 further comprising at least one notch in the inner surface of the first and second cavities, the notch configured to mate with at least one detent on the proximal end of the extenders so as to secure the collar to the extenders when mated.

4. The collar of claim 1 wherein the proximal end of the extenders include a first tong and a second tong position side by side one another and spaced apart from one another, the first and second tongs configured to move from a first position to a second position when compressed towards one another and back to a first position when released, at least one of the first and second tongs containing at least one detent; and the first and second cavities including at least one notch configured to mate with detents on the first and second tongs so that the detents snap into the at least one notch as to releasably attach the collar to said extenders.

5. The collar of claim 4 wherein the first and second cavities are configured to compress said first tong and said second tong towards one another when the proximal end of the extenders are advanced into the first and second cavities of the collar so that the detents mate with the notches and first and second tongs spring back to the first position and releasably attach the extenders to said collar.

6. The collar of claim 4 wherein at least one notch in the first and second cavities extends through the body of the collar to the outside surface thereby providing access to the detent positioned in the notch from the outside surface.

7. The collar of claim 6 further comprising a quick release system having a first arm and a second arm attached to the outer surface of the collar at one end and a surface configured to contact the detent at the other, first arm and second arm disposed about the detents so that compressing first and second the arms towards the outer surface depresses the detent inwardly and disengages the detent from the notch of the collar so as to release the collar from the extenders.

8. The collar of claim 6 wherein said detents are color coded thereby providing visual confirmation when the detents are positioned within the notches and the collar is secured to the extenders.

9. The collar of claim 1 wherein the proximal end surface is configured to mate with at least a portion of a surgical instrument disposed in the passageway thereby aligning the surgical instrument with the passageway of the collar.

10. The collar of claim 1 wherein the stop member is a protrusion configured to contact a proximal end of the extender.

11. The collar of claim 1 wherein the stop member is a solid block configured to contact a proximal end of the extender.

12. The collar of claim 1 wherein first portions of the first cavity are separated from the intermediate cavity by opposing ridges that extend outwardly from the inner surface, the first cavity comprising a second portion that is in communication with the intermediate cavity, the second portion being positioned between the ridges.

13. An extender system comprising:
a first and a second extender extending between a proximal end and a distal end along a longitudinal axis, the first and second extenders forming an inner cavity along the longitudinal axis with openings at the proximal and distal ends, the distal end of the first and second extenders configured to attach to anchors engageable to a spinal column of a patient and the proximal end including at least one detent; and
a collar including a body defining a longitudinal axis, an outer surface and an inner surface configured to define a first cavity, a second cavity and an intermediate cavity disposed therebetween, the inner surface including at least one wall projecting therefrom and being disposed about the intermediate cavity, wherein the first and second cavities receive the proximal end of the extenders to prevent splaying and the intermediate cavity includes a passageway that aligns with the inner cavity formed by the first and second extenders configured for disposal of a surgical instrument,
wherein the first and second cavities further comprise at least one stop member positioned at a proximal end of at least one of the first and second cavities, the stop member being configured to prevent the extenders from protruding out of the proximal end of at least one of the first and second cavities.

14. The extender system of claim 13 wherein a portion of the proximal end has a reduced width relative to the remainder of the extenders, the proximal end configured to fit within the first and second cavities of the collar.

15. The extender system of claim 13 wherein the proximal end of the extenders contain a first tong and a second tong spaced apart from one another along a traverse axis, the first and second tongs configured to move from a first position to a second position when compressed towards one another and back to a first position when released, at least one of the first and second tongs containing at least one detent; and the first and second cavities including at least one notch configured to mate with the detents of the first and second tongs so as to releasably attach the collar to said extenders.

16. The extender system of claim 13 further comprising a quick release system having a first arm and a second arm attached to the outer surface of the collar at one end and a surface configured to contact the detent at the other, first arm and second arm disposed about the detents so that compressing first and second the arms towards the outer surface depresses the detent inwardly and disengages the detent from the notch of the collar so as to release the collar from the extenders.

17. The collar of claim 13 further comprising a top surface configured to mate with at least a portion of a surgical instrument disposed in the passageway thereby aligning the surgical instrument with the passageway of the collar.

18. An extender assembly comprising two extender systems according to claim 13 and at least one capped rod having an elongated portion capped on a first end and a second end, the inner cavity of the extenders configured to receive the capped rod so that the rod is perpendicular to the longitudinal axis of the extenders and the capped ends prevent the capped rod from slipping out of the inner cavity as it is advanced distally towards the spinal column of a patient.

19. A kit comprising:
a collar configured for connection to a proximal end of an extender, the collar comprising a body defining a longitudinal axis, an outer surface and an inner surface configured to define a first cavity, a second cavity and an intermediate cavity disposed therebetween, the inner surface including at least one wall projecting therefrom and being disposed about the intermediate cavity;
at least two extenders extending between a proximal end and a distal end along a longitudinal axis, the first and second extenders forming an inner cavity along the longitudinal axis with openings at the proximal and distal ends, the distal end of the extenders configured to attach to anchors engageable to a spinal column of a patient; and
hardware selected from the group consisting of bone fasteners, screws, and capped rods,
wherein the first and second cavities receive the proximal end of the extenders to prevent splaying and the intermediate cavity includes a passageway configured for disposal of a surgical instrument, and wherein the first and second cavities further comprise at least one stop member positioned at a proximal end of at least one of the first and second cavities, the stop member being configured to prevent the extenders from protruding passed the proximal end of at least one of the first and second cavities.

\* \* \* \* \*